(12) United States Patent
Moore et al.

(10) Patent No.: US 6,849,748 B2
(45) Date of Patent: Feb. 1, 2005

(54) PROCESS FOR THE PRODUCTION OF ANHYDROSUGAR ALCOHOLS

(75) Inventors: Kevin M. Moore, Mt. Zion, IL (US); Alexandra Jan Sanborn, Lincoln, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 102 days.

(21) Appl. No.: 09/955,672

(22) Filed: Sep. 19, 2001

(65) Prior Publication Data

US 2002/0052516 A1 May 2, 2002

Related U.S. Application Data

(60) Provisional application No. 60/244,962, filed on Nov. 1, 2000.

(51) Int. Cl.[7] .......................... C07D 39/22; C07C 69/74; C07C 29/60; C07H 1/00
(52) U.S. Cl. ...................... 549/417; 549/464; 536/18.5; 536/18.6; 536/18.7; 536/55.3; 536/123.1; 536/124; 536/126; 568/902
(58) Field of Search .............................. 536/126, 123.1, 536/124, 18.5, 18.6, 18.7, 55.3; 549/464, 417; 568/902

(56) References Cited

U.S. PATENT DOCUMENTS

| | | | | |
|---|---|---|---|---|
| 3,160,641 A | * | 12/1964 | Hartmann | 549/478 |
| 3,454,603 A | * | 7/1969 | Hartmann | 549/464 |
| 4,297,290 A | * | 10/1981 | Stockburger | 549/478 |
| 4,408,061 A | * | 10/1983 | Salzburg et al. | 549/464 |
| 4,506,086 A | * | 3/1985 | Salzburg et al. | 549/464 |
| 4,564,692 A | | 1/1986 | Feldmann et al. | |
| 4,861,513 A | * | 8/1989 | Lueders et al. | 252/182.24 |
| 2002/0002291 A1 | | 1/2002 | Bhatia et al. | |

FOREIGN PATENT DOCUMENTS

| | | |
|---|---|---|
| DE | 488 602 | 12/1929 |
| GB | 600 870 | 4/1948 |
| WO | WO 00/14081 | 3/2000 |

OTHER PUBLICATIONS

Fleche, G. et al., " Isosorbide: Preparation, Properties, and Chemistry", *Lecture from 36th Starch Convention* (Apr. 24–26, 1985) pp. 1–5; Lestrem, France.

Stoss, P. et al. "1,4:3,6–Dianhydrohexitols", *Advances in Carbohydrate Chemistry and Biochemistry* (1991) pp. 93–173, vol. 49; Academic Press Inc.; Illertissen, Germany.

Goodwin, G. et al. "Preparation of bicyclic hexitol anhydrides by using acidic cation–exchange resin in a binary solvent, 13C–NMR spectroscopy confirms configuration inversion in chloride displacement of methanosulfonate in isomannide and isosorbide derivatives" *Carbohydrate Research* (1980) pp. 133–141; Elsevier Scientific Publishing Company; Amsterdam, Netherlands.

Wiggins, L.F. , "Anhydrides of the Penitols and Hexitols", *Advances in Carbohydrate Chemistry*, (1950) pp. 191–228; Imperial College of Tropical Agricultrue; Trinidad, British West Indies.

Koch, H. et al., "New Industrial Products from Starch", *Starch* (1988) pp. 128–129, vol. 40, Wiley–VCH; Weinheim, Germany.

Bahulayan, D., and Sreekumar, K., "Chiral polyesters with azobenzene moieties in the main chain, synthesis and evaluation of nonlinear optical properties," *J. Mater. Chem.* 9:1425–1429, Royal Society of Chemistry (Jul. 1999).

Bock, K., et al., "Acid Catalyzed Dehydration of Alditols. Part I. D–Glucitol and D–Mannitol," *Acta Chem. Scand.* 35:441–449, Nordic Chemical Societies (1981).

Duclos, A., et al., "A Simple Conversion of Polyols into Anhydroalditols," *Synthesis* 10:1087–1090, Georg Thieme Verlag (1994).

Fléche, G., and Huchette, M., "Isosorbide. Preparation, Properties and Chemistry," *Starch* 38:26–30, VCH Verlagsgesellschaft mbH (1985).

Marr, A., et al., "Synthesis and structure of 1,4:3, 6–dianhydro–2–O– p–tosyl–D–mannitol," *J. Chem. Crystal.* 27:161–166, Plenum Publishing Corporation (1997).

Wiggins, L.F., "The Anhydrides of Polyhydric Alcohols. Part I. The Constitution of isoMannide," *J. Chem. Soc.* 4–6, American Chemical Society (1945).

International Search Report for International Patent Application No. PCT/US01/42880, mailed Apr. 18, 2002.

Marija Morano et al., J. Clin. Invest., vol. 98, No. 2, (Jul. 1996), pp. 467–473.

Masahiko Kurabayashi et al., The Journal of Biological Chemistry, vol. 263, No. 27, (Sep. 25, 1988), pp. 13930–13936.

M.C. Schaub et al., European Heart Journal, vol. 5, (Supplement F), (1984), pp. 85–93.

* cited by examiner

Primary Examiner—Cecilia J. Tsang
Assistant Examiner—Taylor V. Oh
(74) Attorney, Agent, or Firm—Buchanan Ingersoll PC; Craig G. Cochenour; Duane A. Stewart III

(57) ABSTRACT

A process is provided for the preparation of anhydrosugar alcohols. The process involves heating a sugar alcohol or a monoanhydrosugar alcohol starting material in the presence of an acid catalyst, and subsequent purification of the anhydrosugar alcohol. Very high purities are achieved, without the use of organic solvents in the process.

61 Claims, No Drawings

US 6,849,748 B2

PROCESS FOR THE PRODUCTION OF ANHYDROSUGAR ALCOHOLS

This application claims priority to provisional application Ser. No. 60/244,962, filed on Nov. 1, 2000.

FIELD OF THE INVENTION

The present invention relates to the production of anhydrosugar alcohols. More particularly, the present invention relates to a process for the production of anhydrosugar alcohols from sugar alcohols that does not require the use of organic solvents.

BACKGROUND

The chemical formation of closed-ring organic molecules has posed many issues for structural organic chemists. This has been particularly true with regard to synthetic reactions involving sugars and polyols, the acid dehydration of which leads to inernal anhydro compounds (mono- and dianhydro products). Fleche and Huchette, *Staerk*, 38 (1985) 26–30.

The earliest work in this area was done on 1,4:3,6-dianhydro-D-mannitol by Fauconnier in 1884. Only sporadic work followed until the 1940's and 1950's, when intensive work was done on all possible isomers of 1,4:3,6-dianhydrohexitols. Stoss and Hemmer, *Adv. Carbohydrate Chem. and Biochem.* (1991) 93–173. Since then a large body of chemical literature has developed in this area.

The 1,5:3,6-dianhydrohexitols belong to the so-called "biomass-derived substances", obtainable from natural products. Therefore, these compounds are classified as "regenerable resources." Furthermore, 1,4:3,6-dianhydrohexitols, such as isosorbide, can be used as starting materials and intermediates in various organic synthetic reaction schemes. For example, isosorbide is useful in the formation of numerous pharmaceutical compounds, in food production, cosmetic production, plastic and polymer production, and in other industrial uses such as in the production of polyurethane, polycarbonate, polyesters, and polyamides. Stoss and Hemmer, 1991.

Of the known isohexides, isosorbide is considered to be that of the highest importance. Stoss and Hemmer (1991) describe the putative steps leading from D-glucitol (also referred to in the art as sorbitol) to isosorbide. Acidic media are generally used for dehydrating the sugar alcohol substrate. Especially to enhance the yield and to avoid side reactions, certain modifications of the reaction conditions have been employed over the years, with various impacts on yield of isosorbide product. Stoss and Hemmer, 1991.

Several processes for the production of anhydrosugar alcohols (including isohexides such as isosorbide) are known. See, for example, PCT application number PCT/US99/00537 (WO 00/14081), collecting methods and disclosing a continuous production method with recycling of organic solvent. Most methods involve the use of concentrated acids and organic solvents. Goodwin et al. (*Carbohydrate Res.* 79 (1980), 133–141) have disclosed a method involving the use of acidic-cation-exchange resin in place of concentrated, corrosive acids, but with low yield of isosorbide product. An alternative, supersaturation-based method is disclosed in U.S. Pat. No. 4,564,692 (Feldmann et al., Jan. 14, 1986). However, a need continues in the art for a process for production of very pure isosorbide, at reasonable yields, and preferably without the use of potentially hazardous organic solvents.

SUMMARY OF THE INVENTION

The present invention relates to a process for the preparation of anhydrosugar alcohols from sugar alcohol starting materials. The process results in very pure products, with relatively high yields, without the use of organic solvents.

In general, the process involves the heating of the appropriate sugar alcohol starting material, with stirring, until molten; dehydrating the molten starting material in the presence of an appropriate catalyst (e.g., a soluble acid or an acidic ion exchange resin), with stirring, and under vacuum at elevated temperature; purifying the anhydrosugar alcohol, for example by distillation, and then by melt crystallization and/or redistillation; and isolating the final, purified product (for example, by centrifugation or, alternatively, by filtration).

DETAILED DESCRIPTION

The present invention provides a solvent-free process for the production of very pure anhydrosugar alcohols. The process of the invention generally includes the steps of melting a sugar alcohol starting material, maintaining an elevated temperature and adding an appropriate catalyst and applying a vacuum, with stirring, for a length of time (which will depend upon the reaction conditions) sufficient to remove all water. The resultant anhydrosugar alcohol mixture is then subjected to a purification and separation process, and an anhydrosugar alcohol product of high purity is produced.

Typical sugar alcohols, particularly pentites and hexites, are suitable for use as starting materials in the process of the invention. The starting materials can include sugar alcohols, monoanhydrosugar alcohols, or a mixture of such alcohols. Generally the preferred starting materials include arabinitol, ribitol, D-glucitol (also referred to in the art as D-sorbitol or sorbitol, and referred to herein as sorbitol), D-mannitol (or mannitol), galactitol (dulcitol), iditol, and the like. Sorbitol is a particularly preferred starting material because it is readily available, and because pure isosorbide is very useful in a number of chemical and pharmaceutical applications.

In the first step of the process of the present invention, the selected starting material is melted. If, by way of example, sorbitol is the starting material, it is heated to at least about 100° C., or a least to its melting point. For anhydrosugar alcohols generally this temperature is from about 100° C. to about 191°. For sorbitol powder, to provide a specific example, the preferred melting temperature is from about 98° C. to about 100° C. Once molten, the sorbitol is subject to stirring.

A catalyst that will facilitate the dehydration of the sugar alcohol is then added to the molten starting material. Typically the catalysts used to facilitate the dehydration of sugar alcohols are acid catalysts. The classes of acid catalysts useful in the practice of the present invention are soluble acids, acidic ion resins, and inorganic ion exchange materials. Therefore, acids such as sulfuric acid, phosphoric acid, p-toluenesulfonic acid, p-methanesulfonic acid, and the like, are preferred for use in the present invention. Alternatively, for example, Zeolite powders such as CBV 3024 or CBV 5534G (available from Zeolist International), or T-2665 or T-4480 (available from United Catalysis, Inc.), or the like, can be used in the practice of the invention. More preferred are acidic ion resins such as AG50W-X12 from BioRad Laboratories, Amberlyst 15 or 35 from Rohm & Hass, and RCP21H from Mitsubishi Chemical Corp., as well as Dowex 50Wx4 (Dow Chemical Co.). Amberlyst 35 is a particularly preferred resin in the practice of the present invention, specifically for the production of isosorbide from sorbitol.

The amount of catalyst used will vary depending upon the reaction conditions and starting material, as those of skill in the art will appreciate, but will generally be on the order of from about 0.01 equivalents to about 0.15 equivalents by weight. The currently preferred amount of catalyst is 0.1 equivalents by weight.

It is possible to perform one or two dehydrations of the starting sugar alcohol during the reaction, producing a mono- or dianhydrosugar alcohol. The reaction may also be controlled so as to produce a combination of mono- and dianhydrosugar alcohols by adjusting either the reaction conditions or the starting materials, which as those of skill in the art will appreciate, could contain both sugar alcohols and monoanhydrosugar alcohols.

The dehydration in the presence of the catalyst is carried out under a vacuum, at elevated temperatures, and with stirring of the reaction mixture. The vacuum can range over a pressure of from about 0.05 Torr to about 40 Torr, with preferred pressures of from about 1 Torr to about 10 Torr. As a specific example, the currently preferred pressure for the dehydration step in the process of the present invention in which isosorbide is made from sorbitol is from about 1 Torr to about 10 Torr. In the production of isosorbide from sorbitol, the dehydration is carried out for approximately 2 hrs, with constant stirring, at a temperature of about 120° C. The water is pulled off of the melted sorbitol/catalyst mixture under a vacuum of from about 1 Torr to about 10 Torr.

It will of course be appreciated by those of skill in the art that, in a process such as that of the present invention, which involves application of both elevated temperatures and vacuum, the specific parameters of the process, including the time it takes to carry certain steps to completion, will vary depending upon the temperatures and pressures used. As one of skill in the art would anticipate, for example, the inventors have determined that higher vacuum levels for the distillation step gave the expected lower distillation temperature. An additional variable is the selected starting material, which will have a particular melting and/or distillation point (the latter, of course, being dependent upon the vacuum). This is equally true for the purification process described below. However, given the disclosure presented herein, it is within the level of skill in the art to optimize the process parameters of the invention for a particular application. This can be done with only a few preliminary experiments, and without undue experimentation, in light of the instant disclosure.

Following the dehydration procedure, the resultant mixture is purified. In a preferred embodiment, vacuum distillation is used, although alternatives such as filtration, or the addition of activated charcoal with subsequent crystallization, are available. As noted above, the parameters for vacuum distillation will vary depending upon the material to be purified, and the temperature and pressure, as will be appreciated by those of ordinary skill in the art. The pot temperature will of course depend upon the temperature at which the material to be purified distills (the distillation point), which again will depend on the vacuum applied in the system. For example, in the case of isosorbide, a range of vapor temperatures of from about 155° C. to about 170° C. is preferred; more preferred is from about 160° C. to about 170° C.; even more preferred is from about 165° C. to about 170° C. The vacuum pressure can be from about 0.5 Torr to about 40 Torr; preferably from about 1 Torr to about 10 Torr. For example, and specifically with regard to vacuum distillation of isosorbide, a vacuum pressure of from about 1 Torr to about 10 Torr, a pot temperature of about 180° C. and a vapor temperature of from about 160° C. to about 170° C. are currently most preferred.

In order to further purify and isolate the anhydrosugar alcohol, the anhydrosugar alcohol distillate is subjected to melt crystallization. The recovered distillate product is heated to its melting point (e.g., for isosorbide, to approximately 65° C.) until molten, and then cooled over time until the crystallization point is reached, but not so much that the material solidifies. In fact, a slurry-like consistency is preferred, so that the material can be centrifuged. The centrifugation is performed at a relatively high speed for a relatively short period of time, again in order to avoid solidification of the material, and also to avoid having the desired purified anhydrosugar alcohol end product be drawn off with the remaining impurities. The resultant anhydrosugar alcohol product should be at least 98% pure, and in most cases will be >99% pure (depending upon the solidity of the "slurry").

The present invention is described in further detail in the following non-limiting examples.

EXAMPLE 1

This Example describes the production of very high purity isosorbide from sorbitol using a particularly preferred embodiment of the process of the present invention.

Sorbitol powder (180.6 grams, 0.99 mol) was placed in a 3-neck round bottom flask equipped with an agitator, temperature probe, and vacuum line. The sorbitol was heated to approximately 100° C. until molten. An acidic ion exchange resin, Amberlyst 35 (Rhom & Haas) (19.8 grams) was added and vacuum was applied at from about 1 Torr to about 10 Torr. The temperature was increased to from about 120° C. to about 130° C. These temperature and vacuum parameters were maintained for approximately 2 hours, with constant stirring. The resultant mixture was then vacuum distilled at from about 1 Torr to about 10 Torr, pot temperature of 180° C., vapor temperature of 170° C. The distillate was collected and subjected to melt crystallization by heating to approximately 65° C. until molten, then cooling, over about 30 minutes to about 45 minutes to approximately 35° C., at which temperature a slurry-like solution was formed. This solution was then quickly centrifuged (in order to avoid solidification), and the resultant isosorbide product had a purity of 99.3%, with an overall yield of 48%.

EXAMPLE 2

The same apparatus and the same operational conditions-except those specified below—as in Example 1 were used. Upon heating sorbitol to about 100° C. to a molten state, an acidic ion exchange resin, Amberlyst 15 (Robin and Haas, 24.2 g), was added and vacuumed applied (5–7 Torr). Heating was increased to 135° C. and the reaction allowed to stir continuously for about 2 h. The resulting mixture contained 64.5% isosorbide and was then purified by the procedure described in Example 1.

EXAMPLE 3

The same apparatus and the same operational conditions-except those specified below—as in Example 1 were used. Upon heating sorbitol to about 100° C. to a molten state, an acidic ion exchange resin, Dowex 50WX4, (18.1 g), was added and vacuumed applied (7–9 Torr). Heating was increased to 135° C. and the reaction allowed to stir continuously for about 2 h. The resulting mixture contained 64.1% isosorbide. Purification was then performed.

EXAMPLE 4

The same apparatus and the same operational conditions-except those specified below—as in Example 1 were used.

Upon heating sorbitol to about 100° C. to a molten state, an acidic ion exchange resin, Amberlyst 35 (Robin and Haas, 11.7 g), was added and vacuumed applied (9–12 Torr). Heating was increased to 135° C. and the reaction allowed to stir continuously for about 2 h. The resulting mixture contained 18.6% sorbitan and 73.4% isosorbide. The mixture was then purified using the above described procedure.

EXAMPLE 5

The same apparatus and the same operational conditions—except those specified below—as in Example 1 were used. Upon heating sorbitol to about 100° C. to a molten state, an acidic ion exchange resin, RCP21H (Mitsubishi Chemical Corporation, 12.9 g), was added and vacuumed applied (7–9 Torr). Heating was increased to 135° C. and the reaction allowed to stir continuously under vacuum for about 5 h. The resulting mixture contained 68.9% isosorbide. The mixture was then purified using the above described procedure.

EXAMPLE 6

The same apparatus and the same operational conditions—except those specified below—as in Example 1 were used. Sorbitol (221.4 g, 0.99 mol) was heated to about 100° C. to a molten state. At this time, a sulfated zirconia pellet (#416/03 Japan Energy Corporation, 57.7 g) was added and vacuumed applied (5–7 Torr). Heating was increased to 150° C. and the reaction allowed to stir continuously for about 7 h. The resulting mixture contained 2.2% sorbitol, 56.0% sorbitan, and 22.9% isosorbide.

Having now fully described the present invention in some detail by way of illustration and example for purposes of clarity of understanding, it will be obvious to one of ordinary skill in the art that the invention can be performed by modifying or changing the invention with a wide and equivalent range of conditions, formulations and other parameters thereof. Furthermore, it will be obvious to the skilled practitioner that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A process for the purification of an anhydrosugar alcohol, without using organic solvents, the process comprising:
   heating a pentite or hexite sugar alcohol or monoanhydrosugar alcohol starting material, with stirring and without solvents until molten;
   dehydrating the starting material, under vacuum and while maintaining heat and stirring, in the presence of a solid acid catalyst and without solvents to produce a dehydrated anhydrosugar alcohol mixture; and
   purifying the anhydrosugar alcohol without solvents.

2. The process of claim 1, wherein the solid acid catalyst is an acidic zeolite powder.

3. The process of claim 2, wherein the acidic zeolite powder is selected from the group consisting of CBV 3024, 5534G, T-2665, and T-4480.

4. The process of claim 1, wherein the solid acid catalyst is an acidic ion exchange resin.

5. The process of claim 4, wherein the acidic ion exchange resin is selected from the group consisting of AG50W-X12, Amberlyst 35, Amberlyst 15, RCP21H, and Dowex 50Wx4.

6. The process of claim 4 wherein the acidic ion exchange resin is added in an amount giving from about 0.01 to about 0.15 gram equivalents of resin to sugar alcohol.

7. The process of claim 1 wherein the purification comprises vacuum distillation of the dehydrated anhydrosugar alcohol mixture followed by melt crystallization.

8. The process of claim 1 wherein the purification comprises vacuum distillation of the dehydrated anhydrosugar alcohol mixture followed by a re-distillation.

9. The process of claim 1, further comprising a final separation of the dehydrated anhydrosugar alcohol by centrifugation.

10. The process of claim 1, further comprising a final separation of the dehydrated anhydrosugar alcohol by filtration.

11. A process for the production of an anhydrosugar alcohol, without using organic solvents, the process comprising:
    heating a pentite or hexite sugar alcohol or monoanhydrosugar alcohol starting material, with stirring and without solvents until molten;
    dehydrating the starting material, under vacuum and while maintaining heat and stirring, in the presence of an acid catalyst and without solvents to produce a dehydrated anhydrosugar alcohol mixture, wherein the acid catalyst is selected from the group consisting of sulfuric acid, phosphoric acid, p-toluenesulfonic acid, p-methanesulfonic acid, and solid acid catalysts;
    vacuum the distilling the dehydrated anhydrosugar alcohol mixture to produce an anhydrosugar alcohol distillate;
    melt crystallizing the anhydrosugar alcohol distillate without solvents to produce a crystallized anhydrosugar alcohol product; and
    centrifuging the crystallized anhydrosugar alcohol product to produce an anhydrosugar alcohol.

12. The process of claim 11 wherein the dehydration is performed at a temperature of from about 98° C. to about 191° C.

13. The process of claim 11 wherein the dehydration is performed at a temperature of from about 98° C. to about 130° C.

14. The process of claim 11 wherein the dehydration is performed at a temperature of from about 98° C. to about 120° C.

15. The process of claim 11 wherein the dehydration is performed at a vacuum pressure of from about 0.01 Torr to about 40 Torr.

16. The process of claim 11 wherein the dehydration is performed at a vacuum pressure of from about 0.1 Torr to about 10 Torr.

17. The process of claim 11 herein the dehydration is performed at a vacuum pressure of from bout 1 Torr to about 10 Torr.

18. The process of claim 11 wherein the vacuum distillation is performed at a vapor temperature of from about 155° C. to about 170° C. and a pot temperature of at least the distilling point of the dehydrated anhydrosugar alcohol.

19. The process of claim 11 wherein the vacuum distillation is performed at a vapor temperature of from about 160° C. to about 170° C. and a pot temperature of at least the distilling point of the dehydrated anhydrosugar alcohol.

20. The process of claim 11 wherein the vacuum distillation is performed at a vapor temperature of from about 165° C. to about 170° C. and a pot temperature of at least the distilling point of the dehydrated anhydrosugar alcohol.

21. The process of claim 11 wherein the vacuum distillation is performed at a vapor temperature of 170° C. and a pot temperature of at least the distilling point of the dehydrated anhydrosugar alcohol.

22. The process of claim 11 wherein the vacuum distillation is performed at a vacuum from about 0.01 Torr to about 40 Torr.

23. The process of claim 11 wherein the vacuum distillation is performed at a vacuum pressure of from about 0.1 Torr to about 10 Torr.

24. The process of claim 11 wherein the vacuum distillation is performed at a vacuum pressure of from about 1 Torr to about 10 Torr.

25. A process for the production of purified isosorbide, without the use of organic solvents, the process comprising:
heating sorbitol powder at a temperature of about 98° C. to about 105° C., with stirring and without solvents until molten;
dehydrating the melted sorbitol without solvents and by catalysis with an acidic ion exchange resin, added in an amount giving from about 0.01 to about 0.15 equivalents, under vacuum pressure of from about 1 Torr to about 10 Torr, and while maintaining stirring and a temperature of from about 98° C. to about 191° C., to form an isosorbide mixture;
vacuum distilling the dehydrated isosorbide at a pot temperature of approximately 180° C. and a vapor temperature of approximately 170° C., and a vacuum pressure of from about 1 Torr to about 10 Torr, to form an isosorbide distillate;
melt crystallizing the isosorbide distillate by heating the distillate to at least approximately 65° C. and then cooling the distillate, over from about 30 minutes to about 45 minutes, to a temperature of about 25° C. to about 35° C. to form an isosorbide solution having a slurry consistency;
centrifuging the isosorbide solution and;
collecting the purified isosorbide.

26. The process of claim 1 wherein the pentite or hexite sugar alcohol or monoanhydrosugar alcohol starting material is selected from the group consisting of arabinitol, ribitol, sorbitol, mannitol, galactitol, iditol, and mixtures thereof.

27. The process of claim 26 wherein the pentite or hexite sugar alcohol or monoanhydrosugar alcohol starting material is sorbitol.

28. The process of claim 1 wherein said anhydrosugar alcohol is a dianhydrohexitol.

29. The process of claim 28 herein the dianhydrohexitol is isosorbide.

30. The process of claim 1 wherein the dehydration is performed at a temperature of from about 98° C. to about 191° C.

31. The process of claim 1 wherein the dehydration is performed at a temperature of from about 98° C. to about 130° C.

32. The process of claim 1 wherein the dehydration is performed at a temperature of from about 98° C. to about 120° C.

33. The process of claim 1 wherein the dehydration is performed at a vacuum pressure from about 0.01 Torr to about 40 Torr.

34. The process of claim 1 wherein the dehydration is performed at a vacuum pressure of from about 0.01 Torr to about 10 Torr.

35. The process of claim 1 wherein the dehydration is performed at a vacuum pressure of from about 1 Torr to about 10 Torr.

36. The process of claim 7 wherein the vacuum distillation is performed at a vapor temperature of from about 155° C. to about 170° C. and a pot temperature of at least the distilling point of the dehydrated anhydrosugar alcohol.

37. The process of claim 8 wherein the vacuum distillation is performed at a vapor temperature of from about 155° C. to about 170° C. and a pot temperature of at least the distilling point of the dehydrated anhydrosugar alcohol.

38. The process of claim 7 wherein the vacuum distillation is performed at a vapor temperature of from about 160° C. to about 170° C. and a pot temperature of at least the distilling point of the dehydrated anhydrosugar alcohol.

39. The process of claim 8 wherein the vacuum distillation is performed at a vapor temperature of from about 160° C. to about 170° C. and a pot temperature of at least the distilling point of the dehydrated anhydrosugar alcohol.

40. The process of claim 7 wherein the vacuum distillation is performed at a vapor temperature of from about 165° C. to about 170° C. and a pot temperature of at least the distilling point of e dehydrated anhydrosugar alcohol.

41. The process of claim 8 wherein the vacuum distillation is performed at a vapor temperature of from about 165° C. to about 170° C. and a pot temperature of at least the distilling point of the dehydrated anhydrosugar alcohol.

42. The process of claim 7 wherein the vacuum distillation is performed at a vapor temperature of 170° C. and a pot temperature of at least the distilling point of the dehydrated anhydrosugar alcohol.

43. The process of claim 8 wherein the vacuum distillation is performed at a vapor temperature of 170° C. and a pot temperature of at least the distilling point of the dehydrated anhydrosugar alcohol.

44. The process of claim 7 wherein the vacuum distillation is performed at a vacuum pressure of from about 0.01 Torr to about 40 Torr.

45. The process of claim 8 wherein the vacuum distillation is performed at a vacuum pressure of from about 0.01 Torr to about 40 Torr.

46. The process of claim 7 wherein the vacuum distillation is performed at a vacuum pressure of from about 0.1 Torr to about 10 Torr.

47. The process of claim 8 wherein the vacuum distillation is performed at a vacuum pressure of from about 0.1 Torr to about 10 Torr.

48. The process of claim 7 wherein the vacuum distillation is performed at a vacuum pressure of from about 1 Torr to about 10 Torr.

49. The process of claim 8 wherein the vacuum distillation is performed at a vacuum pressure of about 1 Torr to about 10 Torr.

50. The process of claim 11 wherein the acid catalyst is a solid acid catalyst.

51. The process of claim 11 wherein the pentite or hexite sugar alcohol or monoanhydrosugar starting material is selected from the group consisting of arabinitol, ribitol, sorbitol, mannitol, galactitol, iditol, and mixtures thereof.

52. The process of claim 51 wherein the pentite or hexite sugar alcohol or monoanhydrosugar starting material is sorbitol.

53. The process of claim 11 wherein said anhydrosugar alcohol is a dianhydrohexitol.

54. The process of claim 53 wherein the diahydrohexitol is isosorbide.

55. The process of claim 50 wherein the solid acid catalyst is an acidic zeolite powder.

56. The process of claim 55 wherein the acidic zeolite powder is selected from the group consisting of CBV 3024, CBV 5534G, T-2665, and T-4480.

57. The process of claim 50 wherein the solid acid catalyst is an acidic ion exchange resin.

58. The process of claim 57 wherein the acidic ion exchange resin is selected from the group consisting of AG50W-X12, Amberlyst 15, Amberlyst 35, RCP21H, and Dowex 50Wx4.

59. The process of claim 1 wherein the process does not include the step of adding seed crystals.

60. The process of claim 11 wherein the process does not include the step of adding seed crystals.

61. The process of claim 25 wherein the process does not include the step of adding seed crystals.

* * * * *

UNITED STATES PATENT AND TRADEMARK OFFICE
CERTIFICATE OF CORRECTION

| | | |
|---|---|---|
| PATENT NO. | : 6,849,748 B2 | |
| APPLICATION NO. | : 09/955672 | |
| DATED | : February 1, 2005 | |
| INVENTOR(S) | : Kevin M. Moore and Alexandra Jan Sanborn | |

It is certified that error appears in the above-identified patent and that said Letters Patent is hereby corrected as shown below:

On the title page item (56) References Cited, please delete the following references:

"Marija Morano et al., J. Clin. Invest. Vol. 98, No. 2, (Jul. 1996), pp. 467-473.

Masahiko Kurabayashi et al., The Journal of Biological Chemistry, Vol. 263, No. 27, (Sep. 25, 1988), pp. 13930-13936.

M.C. Schaub et al., European Heart Journal, Vol. 5, (Supplement F), (1984), pp. 85-93.".

At Column 6:

Claim 12, line 42, change "C." to --C--.
Claim 14, line 47, change "C." to --C--.
Claim 17, line 56, change "bout" to --about--.
Claim 18, line 60, change "C." to --C-- in both occurrences.
Claim 19, line 64, change "C." to --C-- in both occurrences.

At Column 7:

Claim 20, line 1, change "C." to --C--.
Claim 21, line 4, change "C." to --C--.
Claim 25, lines 18, 19, 26, 27, 29, 30, 34, 36 and 37, change "C." to --C--.
Claim 30, line 54, change "C." to --C--.
Claim 31, line 57, change "C." to --C--.
Claim 32, line 60, change "C." to --C--.

Signed and Sealed this
Twenty-sixth Day of April, 2011

David J. Kappos
*Director of the United States Patent and Trademark Office*

CERTIFICATE OF CORRECTION (continued)
U.S. Pat. No. 6,849,748 B2

At Column 8:

Claim 36, line 6, change "C." to --C-- in both occurrences.
Claim 37, line 10, change "C." to --C-- in both occurrences.
Claim 38, line 14, change "C." to --C-- in both occurrences.
Claim 39, line 18, change "C." to --C-- in both occurrences.
Claim 40, line 22, change "C." to --C-- in both occurrences.
Claim 41, line 26, change "C." to --C-- in both occurrences.
Claim 42, line 29, change "C." to --C--.
Claim 43, line 33, change "C." to --C--.